United States Patent [19]

Assandri et al.

[11] 4,041,168

[45] Aug. 9, 1977

[54] NITROIMIDAZOLE DERIVATIVE WITH ANTIBACTERIAL ACTIVITY

[75] Inventors: Alessandro Assandri, Milan; Giancarlo Lancini, Pavia; Giancarlo Volpe; Bruno Cavalleri, both of Milan, all of Italy

[73] Assignee: Gruppo Lepetit S.p.A., Milan, Italy

[21] Appl. No.: 644,382

[22] Filed: Dec. 29, 1975

[30] Foreign Application Priority Data

Jan. 15, 1975 United Kingdom ............... 01684/75

[51] Int. Cl.² .................. A61K 31/415; C07D 233/91
[52] U.S. Cl. ............................. 424/273; 260/465.5 R; 260/465.5 A; 548/339
[58] Field of Search ...................... 260/309; 424/273

[56] References Cited

U.S. PATENT DOCUMENTS

| | | | |
|---|---|---|---|
| 3,065,133 | 11/1962 | Tchelitcheff | 260/309 |
| 3,287,468 | 11/1966 | Beaman et al. | 260/309 |
| 3,290,328 | 12/1966 | Kollonitsch | 260/309 |
| 3,420,842 | 1/1969 | Lancini et al. | 260/309 |
| 3,472,864 | 10/1969 | Henry et al. | 260/309 |
| 3,584,007 | 6/1971 | Chemerda et al. | 260/309 |
| 3,634,446 | 1/1972 | Hoffer et al. | 260/309 |
| 3,652,579 | 3/1972 | Hoffer et al. | 260/309 |
| 3,828,064 | 8/1974 | Martin et al. | 260/309 |
| 3,954,789 | 5/1976 | Cavalleri et al. | 260/309 |

FOREIGN PATENT DOCUMENTS

| | | | |
|---|---|---|---|
| 741,692 | 4/1970 | Belgium | 260/309 |

OTHER PUBLICATIONS

Matsuura et al. Tetrahedron 1971, vol. 27, pp. 1211–1219.

*Primary Examiner*—Natalie Trousof
*Attorney, Agent, or Firm*—Theodore Post; C. Kenneth Bjork

[57] ABSTRACT

The compound 5-[(1-hydroxy-1-methyl)ethyl]-1-methyl-2-nitroimidazole is valuable in combatting *Trichomonas vaginalis* infections in mammals.

4 Claims, No Drawings

NITROIMIDAZOLE DERIVATIVE WITH ANTIBACTERIAL ACTIVITY

The present invention is concerned with the following 2-nitroimidazole derivative of formula

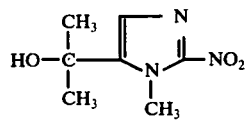

namely 5-[(1-hydroxy-1-methyl)ethyl]-1-methyl-2-nitroimidazole, with the use of this compound as an outstanding antibacterial agent, and with pharmaceutical compositions containing the above compound of formula I as the active ingredient.

A further object of this invention is to provide a method of combatting the infections caused by *Trichomonas vaginalis* in mammals.

The 2-nitroimidazoles are a class of compounds which has been and still is widely investigated both from the chemical point of view, because of the new synthetic approach required for their preparation (G. C. Lancini and Lazzari, Experientia, 21, 83, 1965) and from the pharmacological standpoint, owing to their very interesting antimicrobial properties especially with regard to their remarkable activity against experimental infection by *Trichomonas vaginalis* (G. C. Lancini et al., J. Med. Chem., 12, 775, 1969).

However, the compound of the above formula I, although structurally similar to other 2-nitroimidazoles known from the prior art, is new in itself, as no concrete examples are reported of 2-nitroimidazoles substituted at the 5-position by a hydroxyalkyl group wherein the hydroxy radical is bound to a tertiary carbon directly connected with the imidazole nucleus. For example, alkyl substituted-2-nitroimidazoles are described in U.S. Pat. No. 3,420,842 and U.S. Pat. No. 3,449,967: in this last patent there is also mentioned the corresponding deoxy compound of the above substance of formula I, namely the 5-isopropyl-1-methyl-2-nitroimidazole. South African Pat. No. 4723 discloses, among others, the 5-hydroxymethyl-1-methyl-2-nitroimidazole, wherein the carbon atom which bears the hydroxy group is clearly a primary carbon, whereas Belgian Pat. No. 741,692 covers a generic class of substances represented by the following formula

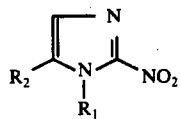

where the substituents $R_1$ and $R_2$ are defined in such a way that when one of them is lower alkyl, the other one is hydroxy-lower alkyl.

Though the compound of the present invention is formally embraced by the foregoing general formula, it is to be noted that in the cited Belgian Patent only concrete examples of 5-hydroxy lower alkyl substituents are reported, wherein the hydroxy lower alkyl groups are 2-hydroxyethyl or 2-hydroxypropyl, i.e. only primary or secondary alcohols are disclosed. The compound of the invention displays very interesting antibacterial properties which can be evidenced through the usual in vitro tests. However, it has an outstanding in vivo activity against the experimental infection in mice caused by *Trichomonas vaginalis*, a protozoa which is responsible of itches and other painful and troublesome diseases of the vaginal tract.

This activity, expressed as an $ED_{50}$ value, is moreover coupled with a very low toxicity, expressed as an $LD_{50}$ value, which was determined substantially according to the method described by Lichtfield and Wilcoxon, Journ. Pharm. Exp. Ther., 96, 99, 1949. In representative experiments, the following results have been obtained:

| Compound | $ED_{50}$ mg/kg mice per os | $LD_{50}$ mg/kg mice per os |
| --- | --- | --- |
| 5-[(1-Hydroxy-1-methyl)ethyl]-1-methyl-2-nitroimidazole | 2.3 | 730 | which indicate that the compound of the invention is a very useful and promising anti-Trichomonas agent. This becomes even more evident if one considers its Therapeutical Index (TI). Said parameter, which is mathematically expressed by the following ratio $LD_{50}/ED_{50}$ gives a reliable idea about the safety of a drug and, considering how it is calculated, it is clear that the higher the TI, the safer the drug is; a high value of the Therapeutical Index means in fact a low effective dose ($ED_{50}$) in comparison with the lethal dose ($LD_{50}$). In the case of the compound of the invention, the Therapeutical Index is 317 which is far higher than that displayed by the best 2-nitroimidazoles so far known. As an example, the 5-isopropyl-1-methyl-2-nitroimidazole, described in U.S. Pat. No. 3,499,967 and therein mentioned as one of the most outstanding in vivo active 2-nitroimidazoles against *Trichomonas vaginalis*, has a Therapeutical Index of 102.

The pharmacological results which have been obtained by investigating the in vivo anti-Trichomonas activity of the compound of the invention are absolutely surprising and could not reasonably be forecast from what is described in the prior art in the field of 2-nitroimidazoles. They are essentially due to the particular (1-hydroxy-1-methyl)ethyl moiety present at the 5-position of the imidazole nucleus, said moiety having the hydroxy radical bound to a tertiary carbon atom which is in turn directly connected with the heterocyclic ring. The role played by the above structure and, consequently, the surprisingly good therapeutical effects which are reached are made clear by the following set of comparative experiments.

1. In the present experiment there are compared the anti-Trichomonas in vivo activities and the Therapeutical Indexes (TI) of the compound of the invention (hereinafter referred to as compound A) and four 5-hydroxy alkyl-2-nitroimidazoles described or falling within prior art patents. In these four compounds the hydroxy group is bound to a primary or secondary carbon atom which not necessarily is linked to the imidazole nucleus. The hereinbelow reported results clearly show that compound A, with its peculiar grouping at the 5-position has a far highest in vivo activity and Therapeutical Index:

TABLE 1

| Compound | ED$_{50}$mg/kg per os mice | LD$_{50}$mg/kg per os mice | TI |
|---|---|---|---|
| B) HO—CH$_2$—[imidazole]—NO$_2$ (N-CH$_3$) | 14.1 | 350 | 24.8 |
| C) HO—CH$_2$—CH$_2$—[imidazole]—NO$_2$ (N-CH$_3$) | 35 | 1500 | 43 |
| D) CH$_3$—CH(OH)—CH$_2$—[imidazole]—NO$_2$ (N-CH$_3$) | 17 | 670 | 39.4 |
| E) HOCH$_2$—CH(CH$_3$)—[imidazole]—NO$_2$ (N-CH$_3$) | 20 | 776 | 38.8 |
| Compound A | 2.3 | 730 | 317 |

Compound B) is described in S.A. Patent 4723.
Compounds C) and D) are described in Belgian Patent 741,692.
Compound E) is embraced by the general formula reported in Belgian Patent 741,692.

Particularly remarkable is the difference between the Theraputical Indexes of compounds A and B in which the hydroxy group is on a carbon atom directly connected to the imidazole nucleus. However, the fact that in compound B the carbon atom bearing the hydroxy group is a primary carbon causes the Therapeutical Index of this substance to be much lower than that of compound A i.e., the compound of the invention.

2. In the following set of experiments there are evaluated the variations of Therapeutical Index (positive or negative) which are observed when some 5-alkyl-2-nitroimidazoles known from the prior art are compared with the corresponding 5-hydroxyalkyl-2-nitroimidazoles, including the new compound A. Obviously all of the compounds are tested for their in vivo activity against *Trichomonas vaginalis*. The aim is again to stress the surprisingly good therapeutical results which are reached with compound A and, moreover, to point out that in the prior art there is no teaching which could lead a skilled technician to foresee these excellent therapeutical results. With reference to the hereinbelow reported table and the first four pair of compounds, the results clearly indicate that the variations of Therapeutical Index which are observed are slightly positive or even negative i.e., that the Therapeutical Index of the known 5-hydroxyalkyl-2-nitroimidazoles either is worse than or is substantially the same as that of the corresponding 5-alkyl compounds: this practically means that no appreciable therapeutical results have been obtained, and that, considering the last pair of substances i.e., compound K and compound A (the compound of the invention), an unrelevant or unfavorable variation of the Therapeutical Index would have to be expected as well. On the contrary, a dramatically favorable and unpredictable variation of this parameter is observed and, clearly, this effect is to be interpreted as a remarkable improvement of the therapeutical (anti-Trichomonas) properties:

TABLE 2
| Compound | ED$_{50}$ mg/kg per os mice | LD$_{50}$ mg/kg per os mice | TI | Compound | ED$_{50}$ mg/kg per os mice | LD$_{50}$ mg/kg per os mice | TI | TI |
|---|---|---|---|---|---|---|---|---|
| K) 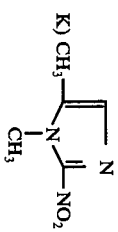 | 10.5 | 246 | 23.4 | | | | | +5.4 |
| G) 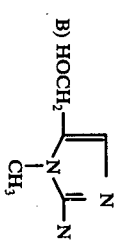 | 9.8 | 372 | 38 | B) 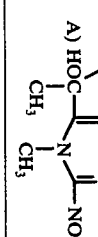 | 14.1 | 350 | 24.8 | +5 |
| H) 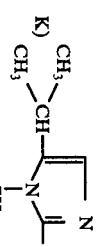 | 26 | 560 | 21.6 | C)  | 35 | 1500 | 43 | +17.8 |
| K) 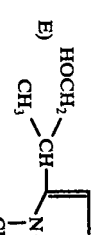 | 2.6 | 265 | 102 | D)  | 17 | 670 | 39.4 | −63.2 |
| K) 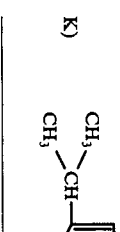 | 2.6 | 265 | 102 | E)  | 20 | 776 | 38.8 | +215 |
| | | | | A)  | 2.3 | 730 | 317 | |

Compounds F thru K are described in U.S. Pat. No. 3,499,967. Compound A is the compound of the present invention. As to compounds B thru E see Table 1 (footnote). TI means Therapeutical Index. ΔTI is the difference between the Therapeutical Index of the 5-hydroxyalkyl and 5-alkyl compounds.

could be reasonably be foreseen that approximately, the same degree of variation should also occur between compound B and compound A. On the contrary, the variation of Therapeutical Index is much more favorable than one could have expected.

TABLE 3

| Compound | ED₅₀mg/kg P.O.mice | LD₅₀mg/kg P.O. mice | TI | Compound | ED₅₀mg/kg P.O. mice | LD₅₀mg/kg P.O. mice | TI | ΔTI |
|---|---|---|---|---|---|---|---|---|
| F) ![structure] | 10.5 | 246 | 23.4 | K) ![structure] | 2.6 | 265 | 102 | 78.6 |
| B) ![structure] | 14.1 | 350 | 24.8 | A) ![structure] | 2.3 | 730 | 317 | 292.2 |

Compounds F) and K) are described in U.S. Patent 3,499,967.
Compound B) is described in South African Patent 4723
Compound A) is the compound of the invention.
TI means Therapeutical Index.
Δ TI is the difference between the Therapeutical Indexes of compounds K) and A and compounds F) and B).

3. In the third experiment there are evaluated the effects on the Therapeutical Index of the substitution with two methyl groups of two hydrogen atoms of the methyl radical at the 5-position of compound F namely

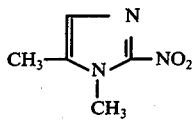

in comparison with the effects on the same parameter caused by the substitution with two methyl groups of the two hydrogen atoms of the hydroxymethyl group of compound B, namely

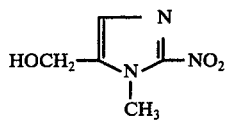

The compounds are obviously tested for their anti-Trichomonas in vivo properties.

This substitution, when carried out on compound F, affords compound K of formula

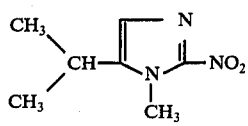

and, when carried out on compound B, affords compound A, namely the compound of the invention. As stated above, compounds F and K are mentioned in U.S. Pat. No 3,499,967, compound B in South African Pat. No. 4723. The obtained results, which are summarized in the hereinbelow reported table further and definitively confirm the important role played by the moiety at the 5-position in compound A and the fact that this gives excellent and unexpected therapeutical results. In fact, considering the variation of Therapeutical Index between compound F and compound K, it The compound of the invention may be administered by various routes; for example, orally, subcutaneously or topically. For oral administration the substance is compounded in such forms as tablets, dispersible powders, capsules, syrups and solutions. Tablets may contain the active ingredient admixed with conventional pharmaceutical acceptable excipients, e.g. inert diluents such as calcium carbonate, sodium carbonate, lactose and talc, granulating and disintegrating agents, such as, for instance, starch, alginic acid and sodium carboxymethylcellulose, binding agents, e.g. starch, gelatin, gum-arabic and polyvinylpyrrolidone and lubricating agents, e.g. magnesium stearate, stearic acid and talc.

Syrups, and solutions are formulated as known in the art. Together with active compound they may contain suspending agents, such as, for instance, methylcellulose, hydroxyethylcellulose, tragacanth and sodium alginate, wetting agents, e.g. lecithin, polyoxyethylene stearates and polyoxyethylene sorbitan monooleate and the common preservative, sweetening and buffering agents.

A capsule or a tablet may contain the active ingredient alone or admixed with an inert solid diluent, such as, for instance, calcium carbonate, calcium phosphate and kaolin.

For the topical administration the active ingredient of formula I is compounded into ointments or vaginal inserts.

The dosage of the compound of formula I effective for combatting the infection by *Trichomonas vaginalis* varies between very wide limits. Generally the best results are obtained when the compound of the invention is administered once a day at a dose of from about 35 to about 100 mg., for ten or more days depending on the severity of the infection. The dosage forms useful for this purpose generally contain from about 35 to about 1000 mg of the active ingredient in admixture with a solid or liquid pharmaceutical acceptable carrier or diluent. The compound of the invention is prepared through a multi-step process representable by the following scheme:

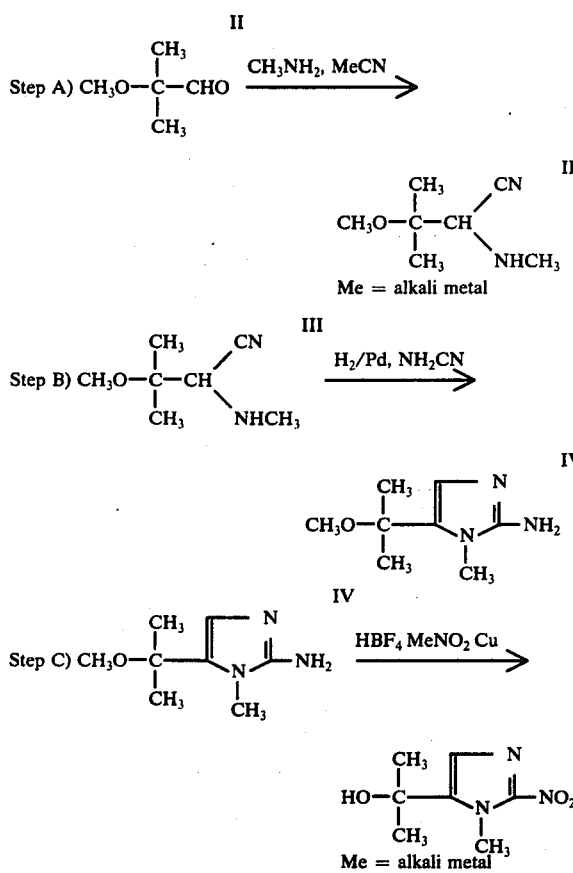

According to step A) of the above illustrate pathway, a molar proportion of the compound of formula II, which is in turn prepared from isobutyraldehyde following the method described in U.S. Pat. No. 3,652,579, is reacted at a temperature of about 5° C with about two-three molar equivalents of methylamine in the presence of water as the reaction solvent, then, after stirring for about one hour at about the same temperature, a molar equivalent of an alkali metal cyanide, e.g. potassium cyanide, is added. Stirring is carried on for about two further hours, while the temperature is kept between 10° and about 15° C, though this range is absolutely not critical. The reaction mixture is finally worked up according to known procedures whereby the compound of formula III, namely, 3- methoxy-3-methyl-2-methylamino-butyronitrile as an oily substance is obtained. Said compound is catalytically hydrogenated in a strong acidic medium at room temperature and atmospheric pressure, according to the first part of Step B). Among the commonly employed hydrogenation catalysts, 10% palladium charcoal is the most preferred one, whereas concentrated hydrochloric acid is conveniently used as the acidic reaction partner. The hydrogenation reaction is carried on until a molar proportion of hydrogen is consumed, then, after filtering the catalyst and adjusting the pH value of the reaction medium to about 4.5-5.0, a slight molar excess of cyanamide is added to the reaction solution, which is heated for about 2 hours at a temperature from about 30° to about 60° C.

The reaction mixture is worked up according to known procedures and a crude oily residue is obtained which is used as such for the subsequent step C). This crude residue essentially consists of the compound of formula IV, namely 2-amino-5-[(1-methoxy-1-methyl)ethyl]-1-methylimidazole, as its acid addition salt, e.g. the hydrochloride if hydrochloric acid is used as the acidic reaction partner, and of impurities which absolutely have no influence on the favorable course of the subsequent step. However, if desired, the compound of formula IV may be characterized by transforming it into a suitable derivative, for instance, an internal salt with picric, trinitrobenzoic or styphnic acid.

The compound of formula IV is finally transformed into the end compound of formula I substantially according to the same procedure outlined in G. B. Pat. No. 1,114,154. This procedure comprises first diazotizing th above 2-aminoimidazole of formula IV with an alkali metal nitrite in concentrated fluoboric acid, and then contacting the obtained diazoderivative with an alkali metal nitrite, in an aqueous medium, in the presence of of copper powder as the catalyst. The reaction is preferably carried out at a temperature comprised between about −20° and about −10° C and is completed within about 4 hours.

The mixture is then worked up following procedures which a skilled technician commonly employes in recovering a product from a reaction medium: said procedures comprise extractions with organic solvents, purification by column chromatography and recrystallization from suitable solvents or solvent systems, whereby the compound of formula I in a pure form is recovered.

It is observed that the scission of the ether function may be uncomplete and therefore together with the compound of formula I, also a small amount of a substance of formula V

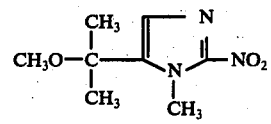

namely 5-[(1-methoxy-1-methyl)ethyl]-1-methyl-2-nitroimidazole, may be transformed into the desired compound of formula I by acid hydrolysis.

Also the compound of formula V has a valuable degree of in vivo anti-Trichomonas activity, even though the Therapeutical Index is not so high as that of the compound of formula I. Representative in vivo tests have given the following results:

| Compound of formula | ED$_{50}$mg/kg per os mice | LD$_{50}$mg/kg per os mice | TI |
|---|---|---|---|
| V | 2.18 | 350 | 160.5 | which, however, demonstrate that also this compound has a far better Therapeutical Index of the best 2-nitroimidazole compound so far known.

The following Examples further illustrate the invention.

EXAMPLE 1

5-[(1-hydroxy-1-methyl)ethyl]-1-methyl-2-nitroimidazole

A. 149.7 Grams (1.465 mole) of α-methoxyisobutyraldehyde (B.p. 95°-100° c) are added dropwise to a solution of 65 g. of sodium metabisulfite in 150 ml. of water, at a temperature comprised between −2° and °C. The resulting mixture is stirred for one hour and is subsequently added with 314 ml of an aqueous solution containing 35% by weight of methylamine (3.25 mole). During the addition of the aqueous solution of methylamine, the temperature raises and is kept at about 5° C by circulating cold water. After stirring for about 1 hour at this temperature, 94.9 g. (1.46 mole) of potassium cyanide are added in a small portions, the resulting mixture is further kept under stirring for about two hours at 10°–15° C and the solid which forms is subsequently removed by filtration. The aqueous filtrate is repeatedly extracted with diethyl ether, then the organic extracts are collected and dried over sodium sulfate. After evaporating the solvent, the obtained residue is purified by distillation under reduced pressure, thus recovering 118 g. of 3-methoxy-3-methyl-2-methylamino-butyronitrile. B.p. 98°–101° C/20 mmHg. The hydrochloride melts at 198°–200° C (from isopropanol).

B. 25.3 Grams (0.178 mole) of the compound prepared under A) are catalytically hydrogenated in a closed system at room temperature and atmospheric pressure, in the presence of 380 ml. of HCl 1N and 3. g. of 10% palladium charcoal. The hydrogenation is carried on for about 2 hours (one molar proportion of hydrogen is consumed during this period) then the catalyst is removed by filtration, the pH of the solution is adjusted to about 4.6 by means of 10% aqueous sodium hydroxide, and 11.5 g. (0.274) mole) of cyanamide are subsequently added. The resulting mixture is heated for 2 hours at about 60° C under vigorous stirring, then is evaporated to dryness and the obtained residue is first extracted with hot diethylether and then with cold absolute ethanol. The ether phase is discarded. After evaporating the ethanol in vacuo, 35 g. of an oily product are recovered which essentially consists of the compound of formula IV, namely 2-amino-5-[(1-methoxy-1-methyl)ethyl]-1-methylimidazole, as the hydrochloride. This compound is used as such for the subsequent step. The picrate of the compound of formula IV sinters at 169°–70° C and melts at 198°–200° C.

C.) 35 Grams of the compound prepared under B) are dissolved in 75 ml of water, then 120 ml. of 40% aqueous fluoboric acid are added.

The mixture is cooled at −20° C, then a solution of 10 g. of sodium nitrite in 40 ml. of water is slowly added during 15 minutes, while stirring. After standing 15 minutes at −10° C-−20° C, the liquid is poured into a mixture of 29 g. of copper powder, 95.2 g. of sodium nitrite and 1400 ml. of water, under vigorous agitation, which is carried on for 1.5 hours. During this phase nitrogen gas is bubbled in the reaction solution. After filtering the pH is adjusted to 2.5 with 10% hydrochloric acid, nitrogen bubbling is carried on for further 30 minutes then the solution is extracted with ethyl acetate.

The organic extracts are washed with 10% aqueous sodium bicarbonate subsequently with water, and are dried over sodium sulfate. After evaporating the solvent a residue is obtained, which is first crystallized from benzene and then purified by column chromatography. 5.9 Grams of the title compound, namely 5-[(1-hydroxy-1-methyl)ethyl]-1-methyl-2-nitroimidazole are recovered. M.p. 160°–62° C.

The benzene mother liquors are brought to dryness and the obtained residue is chromatographed through silicagel by eluting with benzene containing 5% of ethyl acetate (V/V). The obtained fractions are investigated by thin layer chromatography on silicagel. The fractions having $R_f$ value of 0.70 are collected, the solvent is evaporated off and the residue is recrystallized from diethylether/light petroleum. Yield 0.6 g. of the compound of formula V, namely 5-[(1-methoxy-1-methyl)ethyl]-1-methyl-2-nitroimidazole. M.p. 120°–21° C.

The fractions having $R_f$ value 0.43 are collected, the solvent is evaporated off and the residue is recrystallized from benzene. Yield 2.03 g. of the title compound. M.p. 160°–62° C. The obtained 0.6 g. of the compound of formula V are added to 60 ml. of HCl 1N and the resulting mixture is heated at about 80° C until complete solution is observed. After stirring for 10 minutes, the solvent is evaporated in vacuo and a solid is recovered which is recrystallized from benzene. Yield 0.350 g. of the title compound. M.p. 160°–62° C.

EXAMPLE 2

| A capsule is prepared from 5-[(1-hydroxy-1-methyl)ethyl]--1-methyl-2-nitroimidazole | 50 mg. |
|---|---|
| Lactose | 120 mg. |
| Magnesium Stearate | 10 mg. |

EXAMPLE 3

| A vaginal insert is prepared from 5-[(1-hydroxy-1-methyl)ethyl]--1-methyl-2-nitroimidazole | 100 mg. |
|---|---|
| semisynthetic glycerides | q.s. to 2 g. |

EXAMPLE 4

| An 1% ointment is prepared from 5-[(1-hydroxy-1-methyl)ethyl]--1-methyl-2-nitroimidazole | 1 g. |
|---|---|
| Cetostearyl alcohol | 7 g. |
| White petrolatum | 12 g. |
| Liquid petrolatum | 10 g. |
| Tween 60® | 2 g. |
| Span 60® | 2 g. |
| Water | q.s. to 100 g. |

We claim:
1. The compound 5-[(1-hydroxy-1-methyl)ethyl]-1-methyl-2-nitroimidazole.
2. A pharmaceutical composition suitable for combatting infections caused caused by *Trichomonas vaginalis* in mammals, said composition containing from about 35 to about 1000 mg of 5-[(1-hydroxy-1-methyl)ethyl]-1-methyl-2-nitroimidazole in admixture with any pharmaceutical acceptable carrier.
3. A method for combatting the infections caused by *Trichomonas vaginalis* in mammals, which comprises administering an effective amount of 5-[(1-hydroxy-1-methyl)ethyl]-1-methyl-2-nitro-imidazole.
4. A method as in claim 3, wherein the 5-[(1-hydroxy-1-methyl)ethyl]-1-methyl-2-nitroimidazole is administered at a daily dosage varying from about 35 to about 100 mg.

* * * * *